United States Patent
Nordin et al.

(10) Patent No.: US 10,052,183 B2
(45) Date of Patent: Aug. 21, 2018

(54) DENTAL POST AND METHOD FOR ITS FABRICATION

(71) Applicants: Harald Nordin, Chernex (CH); Peter Nordin, Chernex (CH)

(72) Inventors: Harald Nordin, Chernex (CH); Peter Nordin, Chernex (CH)

( * ) Notice: Subject to any disclaimer, the term of this patent is extended or adjusted under 35 U.S.C. 154(b) by 0 days.

(21) Appl. No.: 15/352,638

(22) Filed: Nov. 16, 2016

(65) Prior Publication Data

US 2017/0065383 A1 Mar. 9, 2017

Related U.S. Application Data

(63) Continuation of application No. 12/848,426, filed on Aug. 2, 2010, now Pat. No. 9,526,594.

(30) Foreign Application Priority Data

Aug. 5, 2009 (EP) ..................................... 09167279

(51) Int. Cl.
*A61C 13/30* (2006.01)
*B29C 70/52* (2006.01)
(Continued)

(52) U.S. Cl.
CPC .............. *A61C 13/30* (2013.01); *A61C 13/20* (2013.01); *A61C 19/04* (2013.01); *B29C 70/52* (2013.01);
(Continued)

(58) Field of Classification Search
CPC ........... A61C 13/30; A61C 5/08; A61C 13/20; A61C 19/04
(Continued)

(56) References Cited

U.S. PATENT DOCUMENTS

| | | |
|---|---|---|
| 1,757,595 A | 5/1930 | Siegel |
| 3,557,454 A | 1/1971 | Whitehill et al. |

(Continued)

FOREIGN PATENT DOCUMENTS

| | | |
|---|---|---|
| CA | 2213486 | 9/1996 |
| DE | 3825601 | 3/1989 |

(Continued)

OTHER PUBLICATIONS

European Search Report dated Apr. 20, 3010 issued in corresponding European Patent Application No. 09167279.0.
(Continued)

*Primary Examiner* — Yogesh Patel
(74) *Attorney, Agent, or Firm* — Ostrolenk Faber LLP

(57) ABSTRACT

A dental post has fibre-reinforced material with substantially uniformly directed fibers and mountable in a tooth root canal for fixing a dental prosthetic structure on a tooth stump and a method for its fabrication.

For improving the light conduction properties within the post, at least a fraction of the fibers conduct light, and includes post a tapered portion extending toward its second end. Some of the fibers extend from the first end of said post to the circumferential surface of the tapered portion.

According to a fabrication method of the post a composite structure of uniform cross-section with substantially uniformly directed light conducting fibers in a pultrusion process. At least a portion of the circumferential surface of the composite structure is shaped to provide a tapered portion extending toward the second end of said composite structure.

19 Claims, 3 Drawing Sheets

(51) Int. Cl.
*B29C 70/54* (2006.01)
*A61C 13/20* (2006.01)
*A61C 19/04* (2006.01)
*B29L 31/00* (2006.01)

(52) U.S. Cl.
CPC ..... *B29C 70/545* (2013.01); *B29L 2031/7536* (2013.01)

(58) Field of Classification Search
USPC .................................. 433/220–224, 172–176
See application file for complete search history.

(56) References Cited

U.S. PATENT DOCUMENTS

| | | | |
|---|---|---|---|
| 4,479,783 A | 10/1984 | Weissman | |
| 4,543,065 A | 9/1985 | Bushway | |
| 4,934,936 A | 6/1990 | Miller | |
| 5,104,321 A | 4/1992 | Filhol | |
| 5,275,563 A * | 1/1994 | Cohen | A61C 13/30 433/220 |
| 5,323,263 A | 6/1994 | Schoenmakers | |
| 5,326,263 A * | 7/1994 | Weissman | A61C 5/50 433/220 |
| 5,328,372 A | 7/1994 | Reynaud et al. | |
| 5,820,376 A | 10/1998 | Chalifoux | |
| 5,919,044 A * | 7/1999 | Sicurelli, Jr. | A61C 13/30 433/220 |
| 5,964,592 A * | 10/1999 | Hites | A61C 13/30 433/221 |
| 5,989,032 A | 11/1999 | Reynaud et al. | |
| 6,135,775 A | 10/2000 | Weisman | |
| 6,186,791 B1 * | 2/2001 | Karmaker | A61O 5/35 433/220 |
| 6,371,763 B1 | 4/2002 | Sicurelli et al. | |
| 6,402,519 B1 | 6/2002 | Nordin | |
| 6,439,890 B1 | 8/2002 | Karmaker et al. | |
| 7,331,789 B2 | 2/2008 | Karmaker et al. | |
| 2004/0166472 A1 | 8/2004 | Kangasniemi et al. | |
| 2006/0194172 A1 | 8/2006 | Loveridge | |
| 2007/0072153 A1 | 3/2007 | Gross et al. | |
| 2010/0035214 A1 | 2/2010 | Reynaud et al. | |
| 2011/0129788 A1 | 6/2011 | Lu | |

FOREIGN PATENT DOCUMENTS

| | | |
|---|---|---|
| DE | 20 2010 000 297 | 9/2010 |
| EP | 0260446 | 3/1988 |
| EP | 0370676 | 5/1990 |
| EP | 0522221 | 1/1993 |
| FR | 2874498 | 3/2006 |
| FR | 2882646 | 9/2006 |
| TW | M377205 U1 | 4/2010 |
| WO | WO 96/25119 | 8/1996 |
| WO | WO 96/29017 | 9/1996 |
| WO | WO 2008/107596 | 12/2008 |

OTHER PUBLICATIONS

European Search Report dated Jul. 28, 2015 issued in European Patent Application No. 10171394.

* cited by examiner

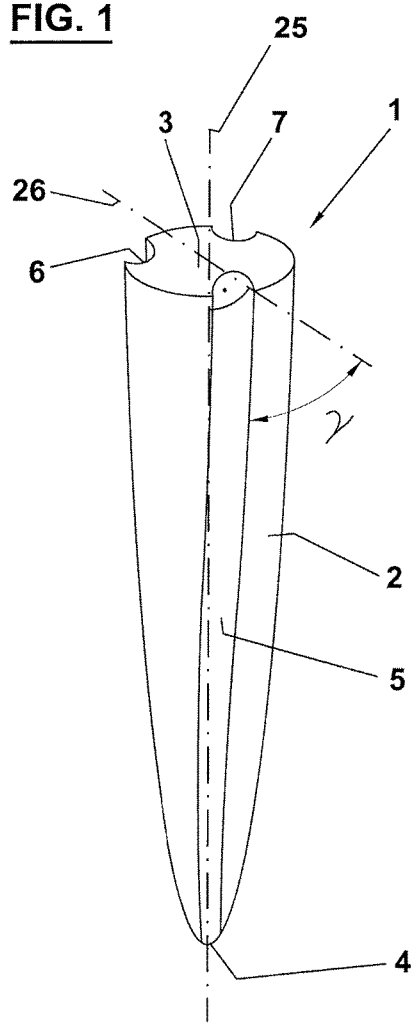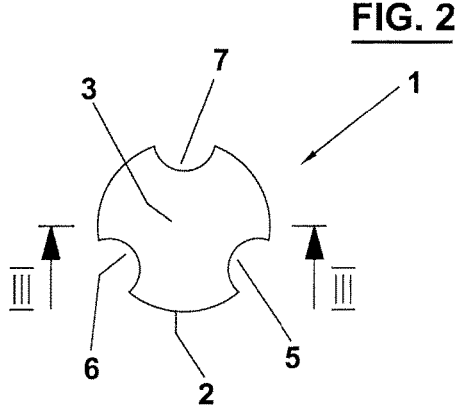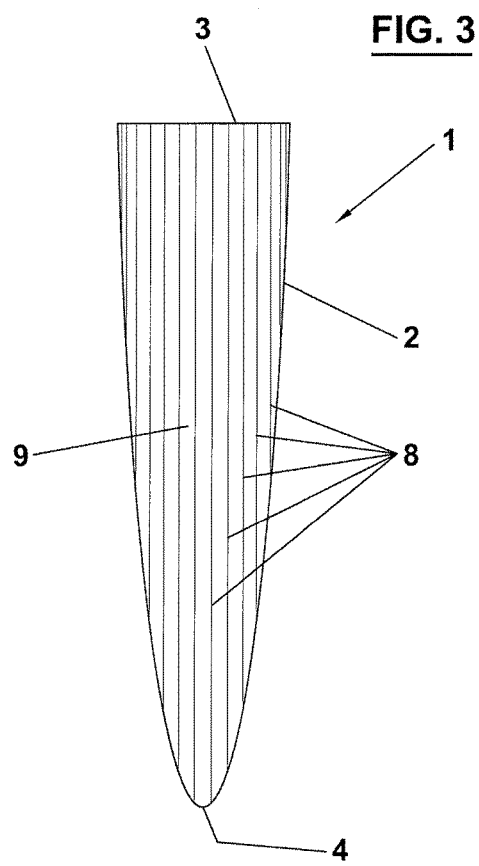

DENTAL POST AND METHOD FOR ITS FABRICATION

CROSS REFERENCE TO RELATED APPLICATIONS

The present application is a continuation under 37 C.F.R. § 1.53(b) of prior U.S. patent application Ser. No. 12/848,426, filed Aug. 2, 2010, which claims priority of European Patent Application No. 09167279.0, filed Aug. 5, 2009. The contents of each of these applications are incorporated in full by reference herein.

FIELD OF THE INVENTION

The invention relates to a dental post consisting of fibre-reinforced material with substantially uniformly directed fibers and mountable in a tooth root canal for fixing a dental prosthetic structure on a tooth stump. The invention further relates to a method for fabricating a dental post consisting of fibre-reinforced material.

BACKGROUND OF THE INVENTION

U.S. Pat. No. 5,919,044 discloses a flexible dental post comprising a bundle of optical fibers that are uniformly directed and twisted in a non-axial arrangement in order to impart additional strength to the dental post. The fiber bundle is embedded in a resin binder and extends from the apical end to the coronal end of the post. In this way, light can be guided in between the two end points of the post. In addition, a transverse light conduction towards the circumferential surface of the post can be achieved by etching or scoring the coating of the fibers yielding several light leakage points along the course of each fiber. The light escaping from these leakage points, however, must pass through the resin binder surrounding the fibers in order to arrive at the circumferential surface of the post. Thus, the choice of material for the resin matrix depends on its good light conduction properties and favorable materials with low transparency may not be applicable.

U.S. Pat. No. 5,989,032 discloses a dental post with a central axis comprising optical fibers embedded in a transparent resin matrix, wherein no particular direction of the fibers is favored. The dental post can be complemented by a truncated cone shaped prosthetic structure which may be a separate piece or formed as an integral part attached to the post. In addition, a setting product for fixing the dental post and the prosthetic core on a tooth stump is disclosed. In order to be transparent to visible light, the setting product may comprise randomly distributed short optical fibers or long optical fibers wound around stiffening elements. Thus, a polymerization of the setting product can be achieved by projecting visible light either directly on the setting product or on the transparent dental post. In the latter case of light being applied on the dental post, a transparent resin material is used for allowing the light conduction within the post. This, however, restricts the choice of available materials for the resin matrix.

Patent application no. DE 38 25 601 relates to a dental device consisting of an apical portion constituting a dental post to be inserted into a tooth stump and a truncated cone shaped coronary portion constituting a prosthetic structure to be arranged on top of the tooth stump. The dental device comprises optical fibers extending from the apical end to the coronary end of the dental post and continuing towards the end surface of the coronary prosthetic structure. Thus, light conduction through the fibers is only possible between the two end points of the dental device and no light can be extracted from the lateral surface of the dental post.

Patent application no. FR 2 874 498 describes a dental post consisting of fiber-reinforced material, wherein fibers and X-ray absorbing particles are embedded in a composite resin matrix. An advantage of the glass or carbon fibers located within the matrix lies in an improvement of the mechanical properties of the post leading to a similar modulus of elasticity as compared to that of the dentine. Besides the mechanical performance of the composites, a high degree of radiopacity and of translucency are important factors to be considered in the design of such a device. In this regard, above cited reference proposes to include X-ray absorbing particles with a size in between 95 nm and 200 nm in the resin matrix in order to allow the resin material to be translucent to light rays with a respective wavelength. Thus, a certain degree of light conduction is ensured within the resin matrix in order to allow light transmission across the interior of said dental post. Furthermore, the described post comprises a tapered structure running with a constant slope in the longitudinal direction and facilitating fitting inside the cavity formed by a tooth root canal.

A disadvantage of this dental post is that no retention means are provided in order to secure the position of the post within the root canal. A further drawback of this dental post is that the exploitation of the resin matrix as a light conductor not only restricts the choice of a preferred X-ray absorbing material in order to avoid the scattering of light rays, but also leads more generally to a certain loss that is related to light diffusion occurring in the resin matrix.

Patent application no. FR 2 882 646 discloses a dental post comprising a conical end portion and a threaded intermediate portion. The advantage of the threaded portion is an improved mechanical retention of the post within the tooth root canal e.g. for preventing an axial or rotational displacement of the post. The proposed slope and shape of the thread is mainly adapted to the intermediate cylindrical surface of the post and does not extend over its conical end portion at which the disposal of such a thread may induce an undesired breaking point. Furthermore, the narrow spacing between adjacent circumferential cycles of the single thread may lead to a large rate of scattering or diffusion of light if applied to a light conducting dental post.

OBJECTS AND SUMMARY OF THE INVENTION

It is therefore an object of the present invention to avoid at least one of the above mentioned disadvantages and to provide the initially mentioned dental post with good optical properties, in particular to provide good light conduction properties and light emission over a comparatively large surface area of the post, by keeping restrictions on the choice of the resin material as low as possible. A further object of the invention is to provide such a dental post with a high degree of radiopacity and/or with photochromic properties by ensuring good optical properties. Another object of the invention is to provide the dental post with good retention properties. Another object of the invention is to provide a method for an advantageous fabrication of such a dental post.

Thus, according to a first aspect of the invention, the dental post comprises a tapered portion extending towards its second end, wherein at least a fraction of the light conducting fibers extend from the first end of the post to the circumferential surface of the tapered portion. In this way, light conduction can be achieved from the first end of the post towards the circumferential surface by means of the light conducting fibers. Thus, the light conducted by means of the fibers can be emitted directly at the circumferential surface. Preferably a major part of light emission from the circumferential surface can therefore be accomplished by means of the fibers and any demands of using a resin material with good light transparency can be lowered. In particular, the light emitted from the circumferential surface may be employed for the polymerisation of a fixation product e.g. on a tooth stump.

Preferably, the tapered portion extends over at least one third, more preferred over at least one half and most preferred over at least two third, of the total length of the post for allowing light extraction from a sufficiently large surface area. In this way, at least a portion of the circumferential surface of the dental post on which a polymerisation product is to be applied may be included within this tapered portion. Advantageously, the tapered portion may extend substantially over the whole length of the post for allowing a good light conduction towards the whole circumferential surface of the post and thus enabling a wide applicability of the dental post. Moreover, the tapered portion preferably comprehends the second end of the dental post for allowing advantageous light extraction in particular from the end portion.

Preferably, at least a fraction of the fibers is adapted for light conduction within the post. Preferably, due to their uniform arrangement within the post, said light conducting fibers are substantially directed from the first end towards the circumferential surface of the post for allowing light conduction by means of the fibers from the first end towards the interior of the post. In this respect an arrangement of fibers may be applicable as disclosed in EP 1 078 608 A1 of the same applicant, which is herewith enclosed by reference. This allows to exploit the superior light conducting properties of fibers, such as glass fibers or optical fibers, as compared to the light conduction through the resin material.

Preferably, the post consists of fibre-reinforced material, wherein the reinforcement fibers may be silica and/or glass and/or carbon and/or quartz fibers. For ensuring the desired optical properties the use of optical fibers, in particular glass and/or silica fibers, as a dominating constituent is preferred.

For facilitating light coupling into the fibers, the invention suggests that ends of the light conducting fibers at the first end of the post are prepared as a light entering surface. This may be achieved by a planar cutting of the fibers. In addition, the fibers may be grinded and/or polished at the first end for achieving a superior coupling. Furthermore, the fibers may be provided with a coating at the first end which allows improved coupling of light into the fibers. Preferably, a fraction of at least 40% and at most 80% in volume of the total content of the dental post is constituted by the fibers in order to ensure sufficient light conduction through the post.

In order to achieve a uniform distribution of light irradiation on the circumferential surface of the post, the fibers are preferably homogeneously distributed within the post. This may imply that the density of fibers per unit volume is approximately constant within the post. Preferably, at least a fraction of the fibers are disposed in parallel with respect to one or more axes extending through the post to allow light conduction in a preferred direction towards the circumferential surface. More preferred, one of these axes is constituted by the longitudinal axis of the post such that at least a fraction of the fibers are longitudinally directed within the post allowing uniform light conduction towards the circumferential surface. In a one-axial arrangement of fibers, at least a major part of the fibers may extend in the longitudinal direction. In a multiaxial arrangement of fibers it is also conceivable that part of the fibers may extend in the longitudinal direction of the post and another fraction of fibers may extend at a certain angle with respect to the longitudinal axis.

Preferably, at least a fraction of the light conducting fibers extend from the first end to the circumferential surface in order to allow light conduction directly to the circumferential surface by means of the fibers. In particular, the invention suggests to use tapering of the circumferential surface, e.g. by cutting the fibre-reinforced material accordingly, in order to connect second ends of the fibers with one respective point of the circumferential surface. In order to allow light extraction from the circumferential surface, the cutting method is preferably adapted to the material properties in order to enable light emission from the fiber ends after cutting. Preferably, the degree of the tapering per unit length—on the average over the whole length of the post—is at least one percent and does not exceed an average angle of conicity of about 35 degrees, more preferred of about 15 degrees.

In order to provide good light emission properties substantially over the whole surface area of the tapered portion, the slope of the taper preferably increases towards the second end of the dental post. More preferred, the taper substantially exhibits a curved shape over its total length resulting in good light emission properties from the surface. In particular, a conical shape of the circumferential surface with a continuously increasing inclination is preferred. Preferably, the taper substantially extends over the whole length of the post in order to allow homogenous light irradiation over the total length of the circumferential surface. Thus, due to the tapered structure and depending on the slope of the taper, the connection of the fibers with the circumferential surface is achieved for allowing light conduction towards the desired points of irradiation.

Preferably, the post is composed of a composite resin matrix. The resin matrix may be constituted by polymers. Preferably, the resin matrix comprises a dimethacrylate compound, more preferred urethane dimethacrylate (UDMA). Such a formulation of the resin matrix may be favoured because of its biocompatibility and in particular for its lack of bisphenol A, a substance commonly used as a resin material which is also suspected to cause cancer. The application of a preferred resin material according to the invention can be possible due to lower demands on the transparency properties of the resin matrix as described above.

Preferably, X-ray absorbing material is embedded in the post, in particular within the resin matrix, for ensuring a high degree of radiopacity. When added to the resin, no scattering of light via the X-ray absorbing material has to be considered in the design of the post for achieving the desired light irradiation properties, due to a direct light conduction towards the circumferential surface by means of the light conducting fibers. Preferably, the X-ray absorbing material consists of discrete particles, in particular metal oxides such as barium oxide and/or fluorinated compounds such as yttrium. It is understood that also carbonates are conceivable for achieving the desired radiopacity.

Preferably, the X-ray absorbing material comprises a mineral filler with a high atomic number. Advantageously, the resin matrix may be loaded with such a mineral filler without impairing or destroying the light conduction properties of the post. According to the invention, this can be achieved by exploiting the above described light conduction through the fibers. In particular, the mineral filler may comprise a chemical compound with an element of an atomic number of at least 37 for providing a desired level of radiopacity. More preferred is an atomic number at least 57, in order to ensure a very high level of radiopacity of the post. Preferably, an ytterbium compound is used as a mineral filler, in particular ytterbium fluoride or ytterbium oxide. In this way, a level of radiopacity equivalent to 400% Aluminium or more may be achieved.

Preferably, photochromic particles are embedded in the post, in particular within the resin matrix, for providing the post with photochromic properties. The photochromic properties may allow an easier identification of the post in a tooth, for instance in the case a reintervention or an extraction of the post is needed. The photochromic particles may be activated by means of LED or Halogen light causing the post to change its color. After turning off the light, the post can return to its natural color, for instance a dentine like color. Advantageously, the resin matrix may be loaded with the photochromic particles without impairing or destroying the light conduction properties of the post. According to the invention, this can be achieved by exploiting the above described light conduction through the fibers.

Preferably, the dental post comprises the X-ray absorbing material and the photochromic particles. For instance, a mixture of above described materials may be used to load the resin matrix. In this way, a proper radiopacity and ease of identification can be achieved by allowing good light conduction properties of the post.

According to a further aspect of the invention, at least one groove may be provided on the circumferential surface of a tapered portion on a dental post, the course of the groove extending in the longitudinal direction of the post and also over only part of its circumference. Such a longitudinal groove may be applicable as a retention means for retaining the dental post in a secured position in the tooth root canal and preventing an axial lift off or rotational displacement of the post and/or the dental prosthetic structure that is to be fixed on the post. Moreover, such a groove may act as an evacuation slot for the resin cement used for fixing the post.

The term "longitudinal" groove refers to the characteristics, that the course of the groove comprises a direction component in the length direction of the dental post. Preferably, the course of the longitudinal groove also includes a direction component in the circumferential direction of the post for providing the desired retention. Preferably, the groove substantially extends over the whole length of the post in order to increase mechanical retention along the total device length.

Such a longitudinal groove may be in particular advantageous with respect to the tapering of the post for avoiding breakage of the post at this particular region. The proposed fraction of the circumference of the surface, along which the course of the groove is extending, allows a disposal of the groove on the tapered portion without risking the breakage of the dental post. More precisely, a breakage of the device may be induced by the choice of a different shape of a groove, such as a thread or similar structure—as confirmed by various experiments previous to the present invention—, since the required amount of thinning down of material establishes a weak point on the tapered portion at which the dental post is prone to break.

A second advantage of a retention groove according to the invention lies in an optimization of the retention properties of the post, wherein a comparatively small portion of the total surface area of the post is affected by the areal coverage of the groove. A favorable result of this limited coverage of the groove with respect to the circumferential surface of the tapered portion lies in a comparatively large surface area with substantially unmodified optical properties. In particular, the good light irradiation properties that can be provided at the tapered portion in the above described manner can be preserved.

Depending on the material properties of the post and the slope and/or the minimum diameter of the tapered portion, also a different structure of a retention groove is conceivable within the scope of the present invention, in particular for a tapered portion with a higher rigidity. For this purpose, the invention suggests that at least one longitudinal groove is provided on the surface which is extending at most twice around the circumference of the surface in order to achieve improved retention properties.

Preferably, several longitudinal grooves according to one of the above described embodiments of a groove are provided on the circumferential surface in order to achieve enhanced retention of the post. More preferred, two to twenty of the grooves are provided and most preferred, two to five grooves are disposed on the surface. In particular, excellent retention properties with insignificant risk of breakage have been demonstrated in a prototype of a dental post with three of the grooves.

Preferably, each of the grooves is extending over a different portion of the circumference in order to equally distribute the mechanical retention of the post around the surface and to minimize a potential risk of breakage originating from circumjacently overlapping grooves. As a further provision for achieving good retention properties, at least three-quarter of the circumference, more preferred substantially the whole circumference, may be covered by the longitudinal grooves.

Preferably, at least one of the grooves exhibits an inclined course with respect to the longitudinal axis of the post for allowing an improved retention of the post. In particular, the groove may have substantially a helical form that is at least partially winding or wrapped around the post. Thus, the groove may exhibit an angle of wrap around the post depending on the length of the post and/or on the fraction of circumference to be covered by the grooves. Preferably, the angle of wrap around the post is at least 50 degrees, more preferred at least 70 degrees, for each groove with respect to a transverse axis normal to the longitudinal axis of the post.

Preferably, at least one of the grooves substantially exhibits a round cross section in order to establish a smooth surface within the groove and to achieve good light irradiation also from the surface portion with the groove. In particular, the groove may present substantially a semicircular structure. The preferred width and/or depth of the grooves is at least 0.01 mm and at most 1 mm, wherein a range in between 0.1 mm and 0.5 mm is more preferred. More preferred, the width and/or depth of the grooves decreases toward the second end of the post in order to further decrease the risk of breakage at the increasing taper. More generally, the cross-sectional size of the grooves may decrease towards the second end of the post. Thus, due to the narrowing of the grooves along the taper of the post, the risk of breaking of the post can be minimized.

Above described grooves are particularly advantageous for such a tapering of a dental post in order to provide improved retention of the post with improved optical properties. It is understood, that the improved retention means stemming from above described longitudinal grooves are also conceivable in a post without light conducting fibers or in a post in which light conduction is not possible through the fibers due to a different fiber arrangement or cutting of the tapered portion. Thus, the present invention is also directed more generally to a dental post with a tapered portion comprising at least one of the longitudinal grooves.

According to another aspect of the invention, a method for fabricating a dental post consisting of fibre-reinforced material is proposed. The method comprises the step of forming a composite structure of uniform cross-section with substantially uniformly directed light conducting fibers in a pultrusion process. Furthermore, the method comprises the step of shaping at least a portion of the circumferential surface of the composite structure to provide a tapered portion extending towards the second end of the composite structure. In this way, at least a fraction of the light conducting fibers extend from the first end of the composite structure to the circumferential surface of the tapered portion.

Preferably, the pultrusion process comprises pulling the fibers through a resin impregnation bath comprising at least one of a X-ray absorbing material and photochromic particles.

Preferably, the circumferential surface is shaped with a turning lathe. Advantageously, various parameters of the turning lathe may be specifically adapted to allow good light emission properties of the fibers at the circumferential surface. In particular, the risk to delaminate the interface between the resin and the fibers may be reduced by a turning speed of the turning lathe in between 8000 and 15000 revolutions per minute. An additional or alternative minimization of delamination effects may be achieved by using a cutting tool with a back rack angle of at least 2° and preferably at most 4°. Delamination may be further reduced by using a cutting tool with an end cutting edge angle of at least 20° 9' and at most 20° 11'. Also a polycrystalline or diamond coating may be applied on the cutting tool for avoiding said delamination effects.

A preferred application of the method comprises the fabrication of a dental post with at least one or a combination of the above mentioned advantageous characteristics.

BRIEF DESCRIPTION OF THE DRAWINGS

The invention will be described in more detail in the following description of a preferred exemplary embodiment with reference to the accompanying drawings. In the drawings:

FIG. 1 is a perspective view of a dental post according to the invention;

FIG. 2 is a front view of the dental post shown in FIG. 1;

FIG. 3 is a lateral sectional view of the dental post shown in FIGS. 1 and 2;

DETAILED DESCRIPTION OF THE PREFERRED EMBODIMENTS

Figure 4:
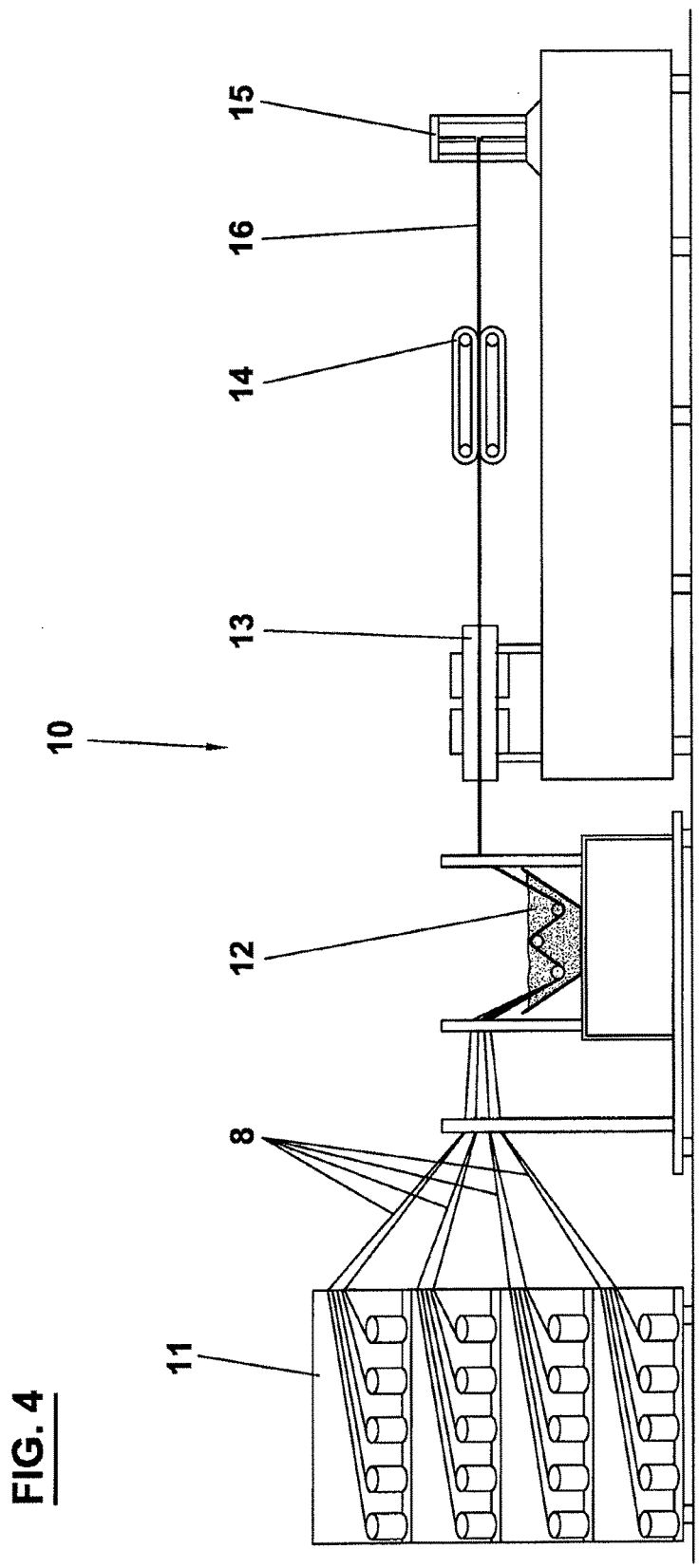
FIG. 4 is a schematic view of a pultrusion system for the fabrication of a dental post according to the invention.

FIGS. 1 to 3 depict a dental post 1 according to an embodiment of the invention. According to the perspective view shown in FIG. 1 and the front view illustrated in FIG. 2, the dental post 1 comprises a circumferential surface 2 with a longitudinal taper extending from the first end 3 to the second end 4 of the post 1. The course of the taper is determined by a continuously increasing slope towards the second end 4. With respect to terms commonly used in dentistry, the first end 3 corresponds to the coronal end and the second end 4 corresponds to the apical end of the dental post.

Three grooves 5, 6, 7 have been formed in the circumferential surface 2, which are longitudinally extending over the total length of the post 1 and twisted along the circumference of the surface 2. FIG. 1 illustrates longitudinal axis 25 and transverse axis 26 of the dental post 1. The twisting of the groove 5 with respect to transverse axis 226 is illustrated as the angle of wrap γ. Thus, each groove 5, 6, 7 extends approximately over one third of the circumference of the surface 2 along a helical course. The grooves 5, 6, 7 are equally distributed around the surface 2, such that each groove is extending over a different portion of its circumference. Moreover, the grooves 5, 6, 7 essentially have a semicircular cross section which size continuously decreases towards the second end 4 of the dental post 1.

The dental post 1 is composed of fiber-reinforced material comprising light conducting fibers 8. According to the sectional view shown in FIG. 3, the course of the fibers 8 within the resin matrix 9 is schematically illustrated. The fibers 8 substantially run longitudinally along the axis of the post 1, such that each fiber arrives at a different point of the circumferential surface 2. In this way, light conducted through the fibers 8 from the first end 3 towards the circumferential surface 2 is emitted from the circumferential surface without passing through the resin matrix 9 of the post 1. An improved light irradiation is in particular achieved due to the increasing slope of the taper towards the second end 4.

The fibers 8 are homogeneously distributed within the post 1 in order to yield a uniform distribution of light irradiation on the circumferential surface 2 of the post 1. At the first end 3 the end portion of fibers 8 are horizontally aligned along a common surface. The fibers 8 comprise a polishing at the first end 3 in order to improve the light coupling characteristics.

The resin matrix 9 is based on urethane dimethacrylate (UDMA). A mineral filler, preferably based on an ytterbium compound, is included in the resin matrix 9 in order to allow radiopacity of the post 1. Furthermore, photochromic particles are included in the resin matrix 9.

FIG. 4 schematically depicts a pultrusion system 10 that is used for an advantageous fabrication of the dental post 1 shown in FIG. 1 to 3. The pultrusion system 10 comprises a series of fiber dispensing racks 11 each providing light conducting fibers 8. The system 10 further comprises a resin impregnation bath 12 containing urethane dimethacrylate (UDMA) that is enriched with a mineral filler, preferably an ytterbium compound, and photochromic particles. A shaping die 13, a conveyor belt 14 and a cutting station 15 is arranged at the end of the pultrusion system 10.

During the pultrusion process, the fibers 8 are pulled through the resin impregnation bath 12 in which the uniformly directed fibers 8 are enriched with the resin material and the shaping die 13 in which the resin is subsequently cured. Pulling is accomplished by the conveyor belt 14. In this way, a composite structure 16 of uniform cylindrical cross-section with substantially uniformly directed light conducting fibers 8 is formed in a continuous manner after passing the shaping die 13. The pultruded composite structure 16 is then cut in the cutting station 15 yielding cylindrical composite structures 17 of a desired length.

Figure 5:
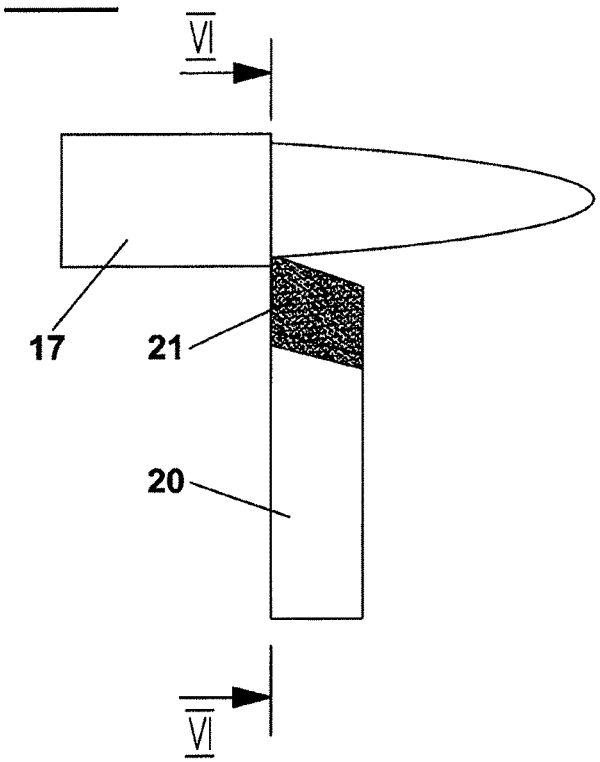
FIG. 5 is a lateral view of a cutting tool according to the invention that is arranged on a composite structure for forming a tapered portion.
Figure 6:
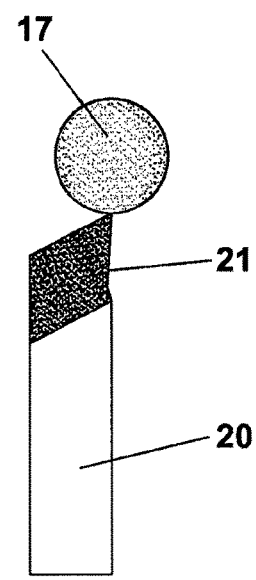
FIG. 6 is a front view of the cutting tool and the composite structure shown in FIG. 5.

As a next step, the composite structure 17 is shaped in order to provide a tapered portion at its circumferential surface. This is accomplished by a turning lathe comprising a cutting tool 20. The shaping process is schematically depicted in FIGS. 5 and 6. FIG. 5 depicts the advancement of the cutting tool 20 along the lateral side of composite structure 17 and FIG. 6 from a front view.

Figure 7:
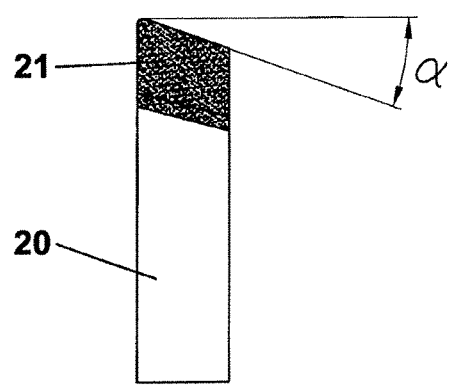
FIG. 7 is a lateral view of the cutting tool shown in FIGS. 5 and 6.
Figure 8:
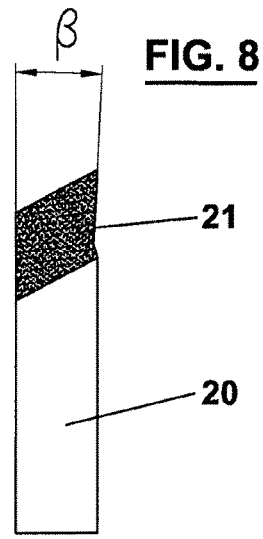
FIG. 8 is a front view of the cutting tool shown in FIG. 5 to 7.

The shaping process is optimized in order to eliminate the risk of deliminating the fiber/resin interface. This is crucial, in particular for providing the desired light emission properties from the fibers 8 at the circumferential surface 2. The optimization parameters comprise a comparatively high turning speed of the turning lathe between 8.000 and 15.000 revolutions per minute. Furthermore specific features on the cutting tool 20 are applied in order to avoid said delamination effects. For this reason, a polychristalline or diamond coating 21 is used on the cutting tool 20. Furthermore, as depicted in the lateral view in FIG. 7, the cutting tool 20 has an end cutting edge angle $\alpha$ of 20° 10'. It has been found that already a small deviation of this angle $\alpha$, such as a conventionally applied angle of $\alpha=20°$ 12', increases the risk of delamination dramatically. The side cutting edge angle of the cutting tool 20 is preferably zero in order to provide a flat side cutting surface. As depicted in the front view in FIG. 8, the back rack angle $\beta$ of the cutting tool 20 has been chosen to be in between 2° and 4° in order to further reduce the risk of delamination due to the impact of the cutting tool 20 on the surface of composite structure 17. Conventionally, a flat back rack angle $\beta$ is applied which leads to a high risk of delamination.

Numerous alterations of the dental post and method for its fabrication described herein will suggest themselves to those skilled in the art. However, it is to be understood that the present disclosure relates to a preferred embodiment of the invention which is for purposes of illustration only and is not to be construed as a limitation of the invention.

The invention claimed is:

1. A dental post configured to be mounted in a tooth root canal for fixing a dental prosthetic structure on a tooth stump, the dental post comprising:
   a fibre-reinforced material comprising a resin matrix and substantially uniformly directed fibers; and
   a tapered portion extending over at least one third of a total length of said dental post towards a second end of said dental post,
   wherein the dental post includes a circumferential surface extending from a first end to a second end of the dental post, the circumferential surface having at least a first circumferential longitudinal groove and a second circumferential longitudinal groove, the first and second circumferential longitudinal grooves extending for an entire length of the dental post in a longitudinal direction of said dental post, the first and second circumferential longitudinal grooves having an inclined course with respect to a longitudinal axis of said dental post, and the inclined course extending along a circumferential direction of the post only over part of said circumferential surface,
   wherein the first circumferential longitudinal groove extends over a different portion of the circumference of the post than the second circumferential longitudinal groove,
   and wherein at least one of the width and the depth of said grooves decreases towards the second end of said post.

2. The dental post according to claim 1, wherein at least one of the grooves comprises a round cross section.

3. The dental post according to claim 2, wherein the round cross section substantially exhibits a semicircular shape.

4. The dental post according to claim 1, wherein at least one of the grooves has a width comprising a value in between 0.01 mm and 1 mm.

5. The dental post according to claim 1, wherein at least one of the grooves has a width comprising a value in between 0.1 mm and 0.5 mm.

6. The dental post according to claim 1, wherein at least one of the grooves has a depth comprising a value in between 0.01 mm and 1 mm.

7. The dental post according to claim 1, wherein at least one of the grooves has a depth comprising a value in between 0.1 mm and 0.5 mm.

8. The dental post according to claim 1, wherein at least one of the first and second longitudinal grooves are at least partially wrapped around the post such that the at least one groove comprises an angle of wrap around said post,
   wherein said angle of wrap is at least 50 degrees with respect to a transverse axis normal to said longitudinal axis of the post.

9. The dental post according to claim 8, wherein said angle of wrap is at least 70 degrees with respect to a transverse axis normal to said longitudinal axis of the post.

10. The dental post according to claim 1, wherein at least one of said first and second longitudinal grooves extends over one third of the circumference of said post.

11. The dental post according to claim 1, wherein at least a fraction of said fibers are adapted for light conduction within said post and at least a fraction of said light conducting fibers extend from the first end of said post to the circumferential surface of said tapered portion.

12. The dental post according to claim 1, wherein a slope of said taper increases towards the second end of said post.

13. The dental post according to claim 1, wherein ends of said light conducting fibers at the first end of said post are prepared as a light entering surface.

14. The dental post according to claim 1, wherein X-ray absorbing material is embedded in said post.

15. The dental post according to claim 14, wherein said X-ray absorbing material comprises a mineral filler comprising a chemical compound with an element of an atomic number of at least 37.

16. The dental post according to claim 1, wherein photochromic particles are embedded in said post.

17. The dental post according to claim 1, wherein said post is further composed of a composite resin matrix comprising a dimethacrylate compound.

18. The dental post according to claim 1, wherein a fraction of at least 40% and at most 80% in volume of the total content of said post is constituted by said fibers.

19. The dental post according to claim 1, wherein said post is further composed of a composite resin matrix comprising urethane dimethacrylate.

* * * * *